US00PP36227P2

(12) United States Plant Patent
Lim

(10) Patent No.: US PP36,227 P2
(45) Date of Patent: Oct. 29, 2024

(54) FLORIBUNDA ROSE NAMED 'ALTsunflower'

(50) Latin Name: *Rosa hybrida*
Varietal Denomination: 'ALTsunflower'

(71) Applicant: Altman Specialty Plants Inc., Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,535

(22) Filed: Sep. 22, 2023

(51) Int. Cl.
*A01H 5/02* (2018.01)
*A01H 6/74* (2018.01)

(52) U.S. Cl.
USPC ..... Plt./145

(58) Field of Classification Search
USPC ..... Plt./141, 145
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of floribunda Rose plant named 'ALTsunflower' is disclosed, characterized by distinctive fully double light yellow flowers with a strong tea rose fragrance. Plants are vigorous and can be grown on their own roots. Plants are compact, semi-upright, flower continuously, and exhibit good resistance to blackspot diseases. The new variety is normally produced as an outdoor garden or container plant.

3 Drawing Sheets

Latin name of the genus and species: *Rosa hybrida.*
Variety denomination: 'ALTsunflower'.

BACKGROUND OF THE INVENTION

The new *Rosa* cultivar is a product of a planned breeding program conducted by the inventor, Peter Lim. The objective of the breeding program was to produce vigorous new garden rose varieties with continuous blooming for ornamental commercial applications. The cross resulting in this new variety was made Jun. 9, 2014.

The seed parent is the variety *Rosa* 'MACrexy', U.S. Plant Pat. No. 6,713. The pollen parent is the variety *Rosa* 'BAline', U.S. Plant Pat. No. 16,659. The new variety was selected in July of 2015 by the inventor in a group of seedlings resulting from the 2014 crossing, in a nursery in Vista, California.

Asexual reproduction of the new cultivar has been performed by vegetative cuttings. This was first performed at a research greenhouse in Vista, California in June 2015 and has shown that the unique features of this cultivar are stable and reproduced true to type in more than 5 successive generations.

SUMMARY OF THE INVENTION

The cultivar 'ALTsunflower' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsunflower' These characteristics in combination distinguish 'ALTsunflower' as a new and distinct *Rosa* cultivar:

1. Compact, bushy floribunda rose.
2. Double yellow flower with on average 30 petals.

3. Early blooming compared to other commercial yellow roses.
4. Continuous flowering.
5. Dark glossy foliage resistant to black spot and powdery mildew disease.
6. Plants can be grown on their own roots; grafting is not required.

PARENT COMPARISONS

Plants of the new cultivar 'ALTsunflower' are similar to plants of the seed parent, in most horticultural characteristics, however, plants of the new cultivar 'ALTsunflower' differ in the following:

1. Flower color of the new cultivar is light yellow, while flower color of the seed parent is pink.
2. Flowers of the new cultivar have fewer petals than flowers of the seed parent.

Plants of the new cultivar 'ALTsunflower' are similar to plants of the pollen parent in most horticultural characteristics, however, plants of the new cultivar 'ALTsunflower' differs in the following;

1. Flower color of the new variety is a lighter yellow than flower color of the pollen parent.

COMMERCIAL COMPARISONS

Plants of the new cultivar 'ALTsunflower' can be compared to the commercial variety *Rosa* 'HARflow', U.S. Plant Pat. No. 10,478. These varieties are similar in most horticultural characteristics, however 'ALTsunflower' differs in the following:

1. Flower color of the new variety is light yellow, while flower color of this comparator is orange-yellow.
2. Flowers of the new variety are smaller than flowers of this comparator.

Plants of the new cultivar 'ALTsunflower' can also be compared to the commercial variety *Rosa* 'KORresia', U.S. Plant Pat. No. 3,509. These varieties are similar in most horticultural characteristics, however 'ALTsunflower' differs in the following:

1. Plants of the new variety are not as tall as plants of this comparator.
2. Flowers of the new variety have more petals than flowers of this comparator.

BRIEF DESCRIPTION OF THE PHOTOGRAPHS

The accompanying photograph in FIG. 1 illustrates in full color a close up of an individual flower of 'ALTsunflower' on a plant of approximately 2-years old.

Figure 1:
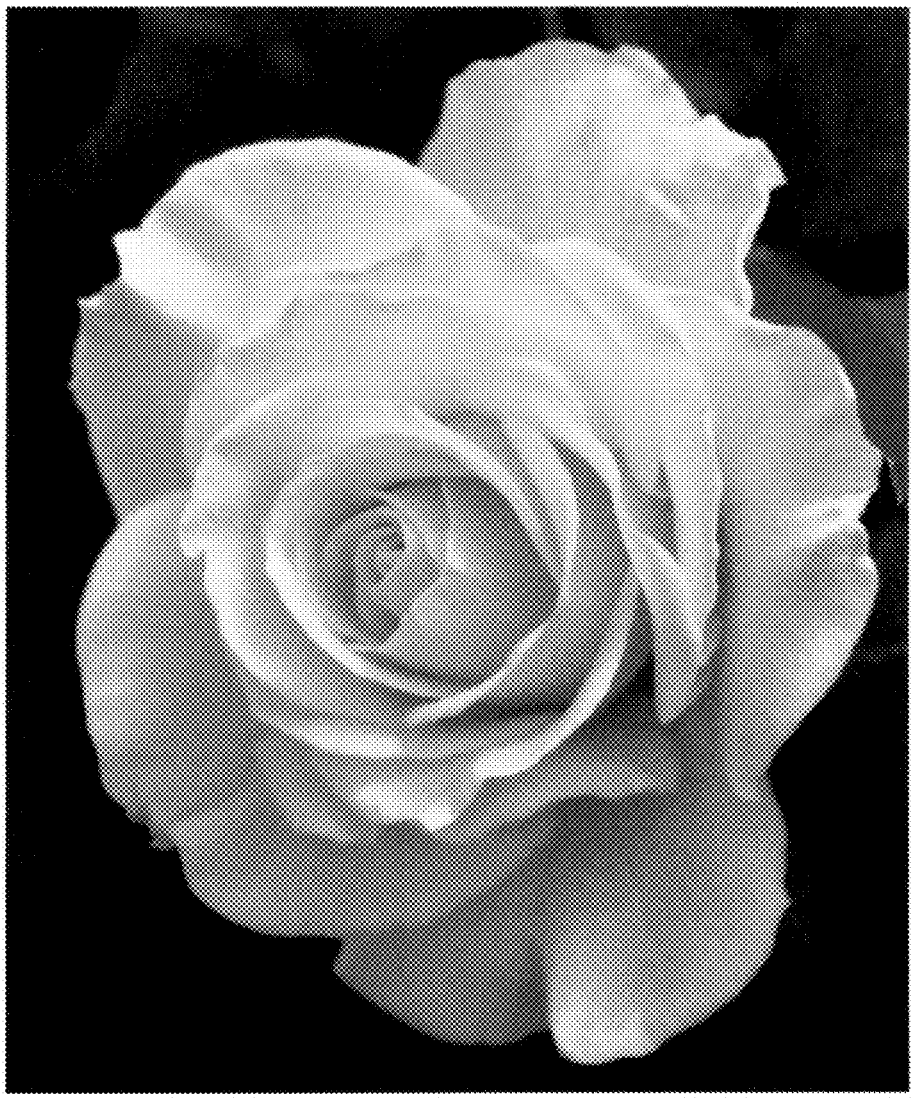
Figure 2:
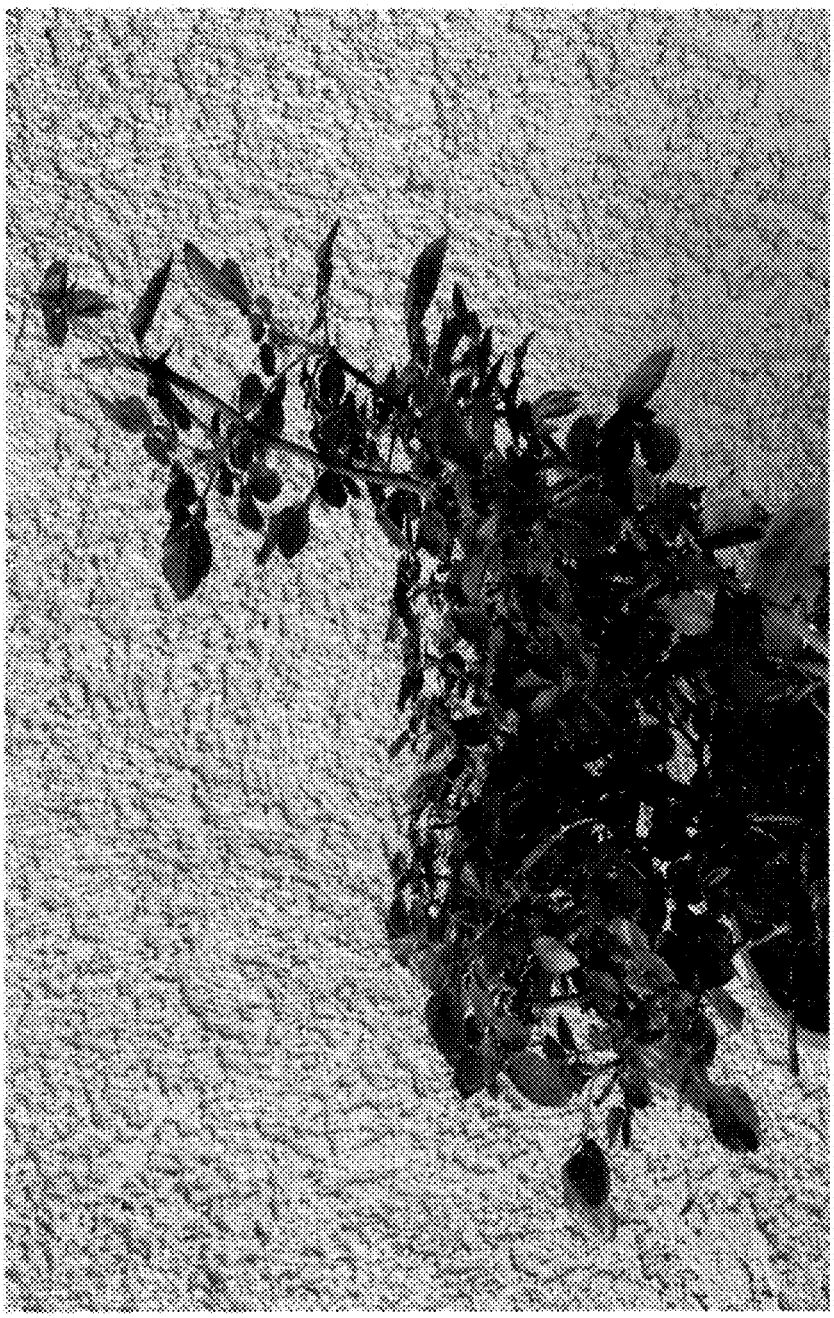
FIG. 2 is a plant of 'ALTsunflower', photographed in April in Southern California, showing plant form and foliage at approximately 2.5 years.
Figure 3:
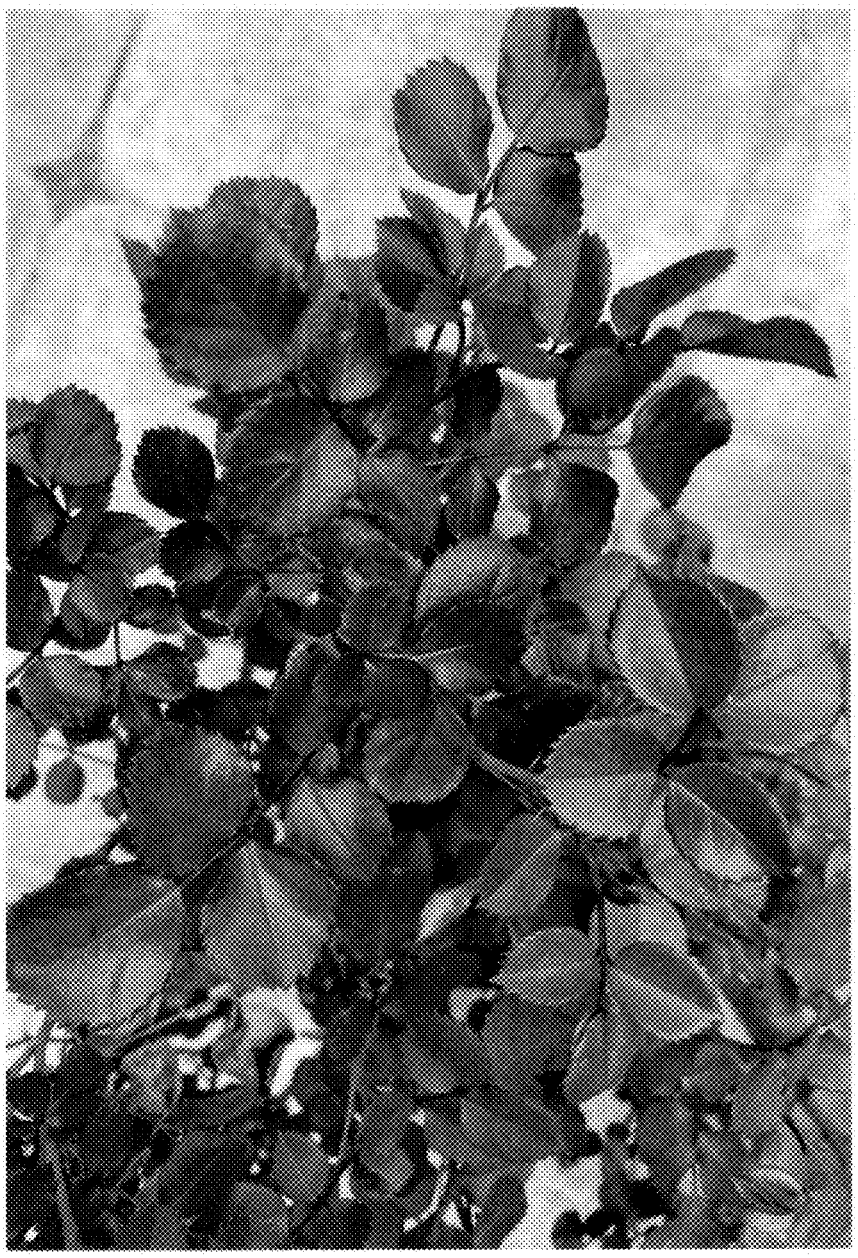
FIG. 3 is a close-up view of the foliage of the new variety.

The photographs were taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTsunflower' plants grown outdoors in Palm Desert, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTsunflower'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact. Semi-upright to intermediate, outwardly spreading.

Container size: 2-gallon.

Height: 35 cm.

Plant spread: 50 cm.

Rootstock: Own root.

Growth rate: Moderate.

Branching characteristics: Sympodial branching.

Length of primary lateral branches: Average range 10 to 25 cm.

Diameter of lateral branches: Approximately 4 to 5 mm.

Quantity of branches: 6 to 8 main branches, moderate lateral branches, 8 to 10 lateral branches per main branch.

Branches-young wood:

*Diameter*.—Approximately 4 mm.

*Texture*.—Glabrous.

*Approximate density/quantity of prickles*.—Infrequent full size prickles.

*Color*.—Near RHS Green 143C.

Branches-old wood:

*Diameter*.—Approximately 5 to 7 mm.

*Color*.—Near RHS Yellow-Green 144B, striped Greyed-Green 195B.

*Texture*.—Glabrous. Oldest, basal growth scaly.

Prickles:

*Approximate density/quantity of prickles*.—Young growth: Sparse, 1 per linear 3 to 5 cm. 5 to 10 mm long, base near 3 to 4 mm. Spike-like. Colored near RHS Greyed-Orange N167C. Mature growth: Moderate, irregularly occurring. Approximately 5 mm in diameter at base. 7 mm long. Colored near RHS Greyed-Orange 165A.

FOLIAGE

Leaf:

*Arrangement*.—Alternate and compound.

*Quantity*.—Average 8 to 14 per main branch.

*Internode*.—Average range 2 to 3.5 cm.

*Length*.—Approximately 8 to 11 cm.

*Width*.—Approximately 5 to 9 cm.

Rachis:

*Length*.—Approximately 3 cm.

*Diameter*.—Approximately 2 mm.

*Color*.—Upper surface: Near RHS Yellow-Green 144C. Lower surface: Near RHS Yellow-Green 144B.

*Texture*.—Glabrous. 1 to 3 small, sharp prickles.

Leaflet:

*Quantity*.—5 per leaf.

*Length*.—Approximately 4 cm to 6 cm.

*Width*.—Approximately 3 cm to 4 cm.

*Shape of blade*.—Broad ovate.

*Apex*.—Acute.

*Base*.—Broadly rounded.

*Margin*.—Finely serrate.

*Appearance of top surface*.—Very glossy.

*Appearance of bottom surface*.—Matte.

*Texture of top surface*.—Glabrous.

*Texture of bottom surface*.—Glabrous.

*Color*.—Young foliage upper side: Near RHS Green 137A. Very thin Greyed-Purple 187B on margin serrations. Young foliage under side: Near RHS Green 138A. Very thin Greyed-Purple 187B on margin serrations. Mature foliage upper side: Near RHS Green 139A. Mature foliage under side: Near RHS Green 137D.

*Venation*.—Type: Reticulate. Venation color upper side: Near RHS Green 137C. Venation color under side: Near RHS Green 137D.

Petiole:

*Length*.—Approximately 1.5 to 2.2 cm.

*Diameter*.—Approximately 3 mm.

*Texture*.—Glabrous.

*Color*.—Upper surface: Near RHS Yellow-Green 144C. Lower surface: Near RHS Yellow-Green 144B.

*Petiole wing*.—Typically 9 mm long and 5 mm wide. Apex apiculate. Upper surface colored near RHS Yellow-Green 144B, lower surface colored near Yellow-Green 144A. Texture: Glabrous.

FLOWER

Natural flowering season: Spring until Autumn.
Inflorescence type and habit: Fully double rotate flowers.
Rate of flower opening: Approximately 7 days from bud to fully opened flower.
Flower longevity on plant: About 10 days, after fully opened.
Quantity of flowers: 10 to 20 fully opened flowers and buds.
Flower size:
*Diameter*.—Approximately 8 to 9 cm.
*Height*.—Approximately 4 cm.
Flower shape:
*From above*.—Round to very slightly irregular round.
*Profile of upper part of flower*.—Flattened convex.
*Profile of lower part of flower*.—Flattened convex. Lower petals reflexing moderately with age.
Peduncle:
*Length*.—3 to 4 cm.
*Diameter*.—4 mm.
*Color*.—Near RHS Green 143C.
*Texture*.—Glabrous.
Petals:
*Arrangement*.—Multiple rotate, overlapping whorls.
*Quantity*.—Average 30.
*Length*.—3 to 4 cm.
*Width*.—2.3 to 3.2 cm.
*Shape*.—Obovate.
*Margin*.—Entire. Rolls under moderately.
*Apex*.—Rounded with 2 to 5 irregular shallow notches.
*Base*.—Very broad attenuate.
*Texture*.—Glabrous all surfaces.
*Color*.—When opening: Upper surface: Near RHS Yellow 4C flushed 4A. Very small basal blotch near 6A. Lower surface: Near RHS Yellow 4C flushed 4A. Very small basal blotch near 5A. Fully opened: Upper surface: Near RHS Yellow 4C flushed 4A. Very small basal blotch near 6A. Lower surface: Near RHS Yellow 4C flushed 4A. Very small basal blotch near 5A. Aging: Upper surface: Near RHS Yellow 4C flushed 4B. Very small basal blotch near 5A. Lower surface: Near RHS Yellow 4D flushed 4B. Very small basal blotch near 5A.
Bud:
*Shape*.—Conical.
*Length*.—Approximately 2.9 cm.
*Diameter*.—Approximately 2.0 cm.
*Color*.—Near RHS Yellow 6C.
Sepals:
*Quantity*.—5.
*Length*.—2.5 cm.
*Width*.—1 0 mm.
*Shape*.—Narrow deltoid.
*Apex*.—Apiculate. No sepal extensions.
*Margin*.—Entire.
*Texture*.—Slightly pubescent lower surface, densely and softly pubescent upper surface.
*Color*.—Interior Surface: Near RHS Green 138B, flushed 138C. Exterior Surface: Near RHS Green 138A, flushed 137D.
Receptacle:
*Depth*.—5 mm.
*Diameter*.—8 mm.
*Shape*.—Flat.
*Color*.—Near RHS Yellow-Green 145D.
Fragrance: Strong floral tea rose scent.

REPRODUCTIVE ORGANS

Stamens:
*Quantity*.—Average 70.
*Filament length*.—Approximately 4 to 9 mm.
*Filament color*.—Near RHS Yellow 4B.
Anthers:
*Length*.—2 mm.
*Shape*.—Oblate
*Color*.—Near RHS Greyed-Purple 183A.
*Pollen*.—Scant, colored near RHS Greyed-Orange 166B.
Pistil: Misshapen 3-parted structure in center of receptacle. About 3 mm in length and 3 mm in diameter. Colored near RHS Yellow-Green 145D.

OTHER CHARACTERISTICS

Seeds and fruits: Not observed.
Disease/pest resistance: Good overall disease resistance to normal pests and diseases typical of garden roses. Very good resistance to blackspot diseases.

What is claimed is:

1. A new and distinct cultivar of floribunda Rose plant named 'ALTsunflower' as herein illustrated and described.

* * * * *